(12) United States Patent
Andersson

(10) Patent No.: US 7,229,833 B1
(45) Date of Patent: Jun. 12, 2007

(54) METHOD AND A DEVICE FOR MEASURING, BY PHOTO-SPECTROMETRY, THE CONCENTRATION OF HARMFUL GASES IN THE FUMES THROUGH A HEAT-PRODUCING PLANT

(76) Inventor: Christer Andersson, Nottovagen 109, Karlholmsbruk (SE) SE-810 64

( * ) Notice: Subject to any disclaimer, the term of this patent is extended or adjusted under 35 U.S.C. 154(b) by 539 days.

(21) Appl. No.: 10/110,164

(22) PCT Filed: Sep. 27, 2000

(86) PCT No.: PCT/SE00/01866

§ 371 (c)(1),
(2), (4) Date: Apr. 9, 2002

(87) PCT Pub. No.: WO01/27593

PCT Pub. Date: Apr. 19, 2001

(30) Foreign Application Priority Data

Oct. 12, 1999 (SE) .................................. 9903656

(51) Int. Cl.
*H01N 31/00* (2006.01)
(52) U.S. Cl. .................. 436/73; 436/119; 436/164; 422/83; 422/91; 422/94
(58) Field of Classification Search .................. 422/83, 422/91, 94, 54; 436/119, 164, 167, 171
See application file for complete search history.

(56) References Cited

FOREIGN PATENT DOCUMENTS

| SE | 9402300 | * 12/1995 |
|----|---------|-----------|
| WO | WO 86/07455 | 12/1986 |

OTHER PUBLICATIONS

Optical and laser remote sensing /ed. : D. K. Killinger and A. Mooradian Berlin Springer 1983 (Springer series in optical sciences, 0342-4111; 39) figure 1.

* cited by examiner

*Primary Examiner*—Jill Warden
*Assistant Examiner*—Sam P. Siefke
(74) *Attorney, Agent, or Firm*—Young & Thompson

(57) ABSTRACT

A method for measuring the concentration of harmful gases in flue gases through a heat-producing plant that includes a combustion space and a device located downstream of the combustion space, the device includes tubes, through which for instance water, steam or air may pass in order to be heated by heat transfer from flue gases formed during the combustion. In a region near the tube device, at least one beam of ultraviolet light is emitted from a light emitter at one side of a flue gas duct to a light receiver located at the opposite side of the duct, which light emitter is connected to a spectrometer cooperating with a computer unit, in which spectrometer the light is divided spectrally.

12 Claims, 4 Drawing Sheets

Figure 1:
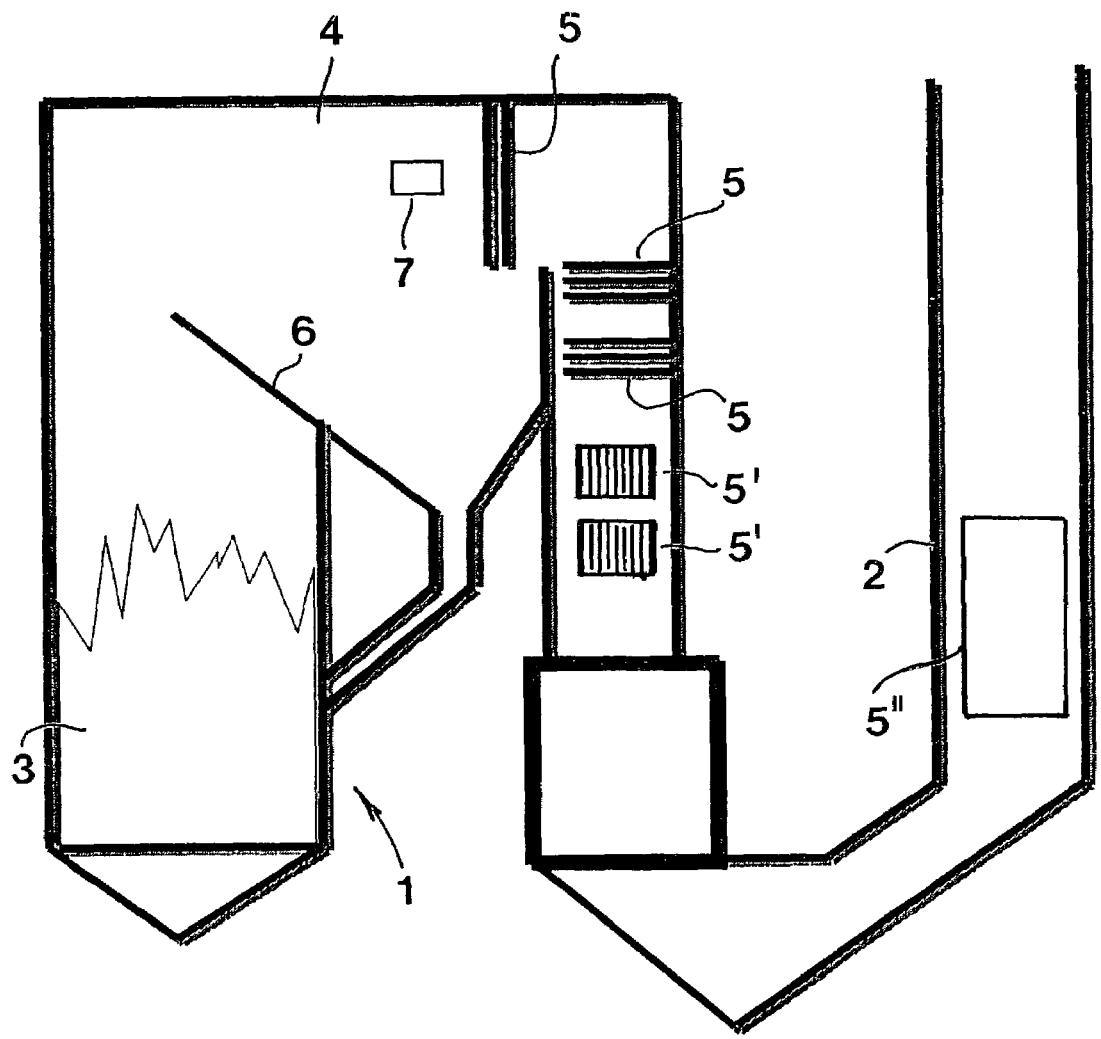

METHOD AND A DEVICE FOR MEASURING, BY PHOTO-SPECTROMETRY, THE CONCENTRATION OF HARMFUL GASES IN THE FUMES THROUGH A HEAT-PRODUCING PLANT

TECHNICAL FIELD OF THE INVENTION

The present invention relates to a method and a device for measuring, by photo-spectrometry, the concentration of harmful gases in the flue gases through a heat-producing plant of the kind that comprises a first space for the combustion of a fuel, a device placed in a second space located downstream of the combustion space, said device in the second space comprising tubes through which a medium, such as water, air or steam, may pass in order to be heated by heat transfer from the flue gases formed during the combustion, and a chimney located downstream of the tube device for letting out the flue gases from the plant.

BACKGROUND OF THE INVENTION AND PRIOR ART

Simultaneous production of heat and steam by combustion of a so-called bio-fuel, i.e., a solid fuel consisting of wood or biomass, has lately become more and more common, inter alia due to the facts that such a production is power-efficient, shows endurance in the long run, may be based on domestic raw materials and gives a minimal influence on the environment. However, it has turned out that the combustion of bio-fuel is a process that in some respects is more complicated and difficult to handle than the combustion of other solid fuels, such as coal. One complication is that the ashes from a bio-fuel has another composition and other melting properties than, e.g., coal ash. Inter alia, this difference involves costly problems with corrosion and ash deposition on the tubes included in existing superheating plants. Thus, serious high temperature corrosion has been observed in the major part of combined power and heating plants in Sweden after some years of operation with 100% bio-fuel. The problems may become particularly accentuated when to the fuel are added such materials as demolition timber and sorted waste of different types. In practice, the corrosion manifests itself in that the usually high-alloyed, and thereby expensive, superheater tubes are coated with stout, strongly adhering layers or deposits of ash, at the same time as the tube surface underneath is exposed to corrosive melts which give rise to a loss of metal.

Among experts, unanimity reigns that chlorine constitutes the main corrosion accelerator in the above-mentioned context. A conventional theory is that chlorine is transported into the ash deposit on the superheater tubes in the form of gas phase potassium chloride (KCl), alternatively as very small aerosols of potassium chloride that have condensed immediately upstream of the superheater device. Thereafter, a reaction with sulphur takes place on the tube surface in the ash deposit, thereby forming potassium sulphate and free chlorine, which in this form is very corrosive. Albeit this theory is plausible, in practice great difficulties exist not only to verify this theory but also to take measures to solve the problem, above all due to the lack of a suitable measuring technique. It is true that in SE 8502946-0, it is in general terms described how photo-spectrometry may be utilized to determine certain parameters, e.g., the concentration, for gaseous substances that occur in such combustion processes that are performed at high temperatures, but in this case the technique is primarily focussed on measuring in flames, and the document does not contain any instructions as to how the technique would, in practice, be used for measurements in plants of the type presented in the preamble.

Quite generally, in heat-producing plants occur, besides the above-mentioned corrosion problems, also other similar problems that are caused by the presence of gaseous metal chlorides or metals in elementary form. Hence, in the plants may be included also other arrangements than merely superheater devices comprising sets or packages of tubes, through which for instance air is circulated in order to be heated (in practice, such arrangements usually consist of air pre-heaters or so-called economizers). When metals, such as heavy metals in the form of zinc and lead in gaseous form, are carried by the flue gases and hit the arrangements, they are deposited on the surfaces of the tubes, thereby forming deposits that are not necessarily corrosive, but that deteriorate the heat transfer from the flue gases to the medium that circulates within the tubes.

OBJECTS AND FEATURES OF THE INVENTION

The present invention aims at overcoming the shortcomings associated with previously known measuring technique and in a purposeful way eliminating or counteracting the corrosion and deposit problems that arise in tube-including devices for heat transfer, e.g., superheater devices, economizers or air pre-heaters that exist downstream of the combustion space in combustion plants. Therefore, a primary object of the invention is to create a process as well as a device which in practical operation at difficult external conditions manage to specifically determine the presence and concentration of exactly those gaseous substances in the flue gases of the combustion process which give rise to serious corrosion or harmful deposits on the tubes that are included in said devices. Another object is to provide a process, by means of which the very creation of corrosive or harmful gases in the flue gases that shall pass through the tube devices may be restrained.

According to the invention, at least the primary object is attained by the characteristics given in the characterizing clauses of claims 1 and 5. Advantageous embodiments of the invention are further defined in the dependent claims.

BRIEF DESCRIPTION OF THE APPENDED DRAWINGS

In the drawings

Figure 2:
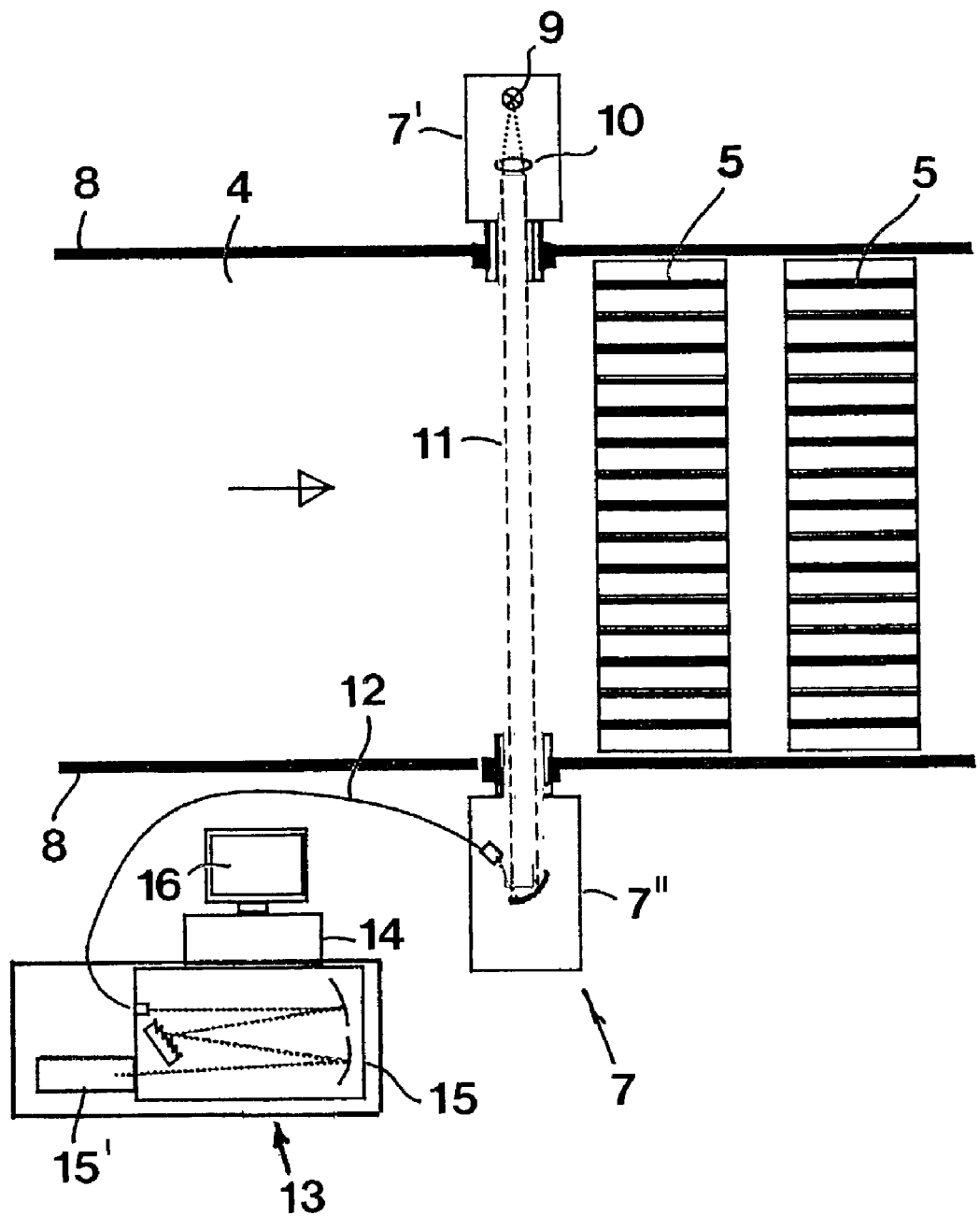
Figure 3:
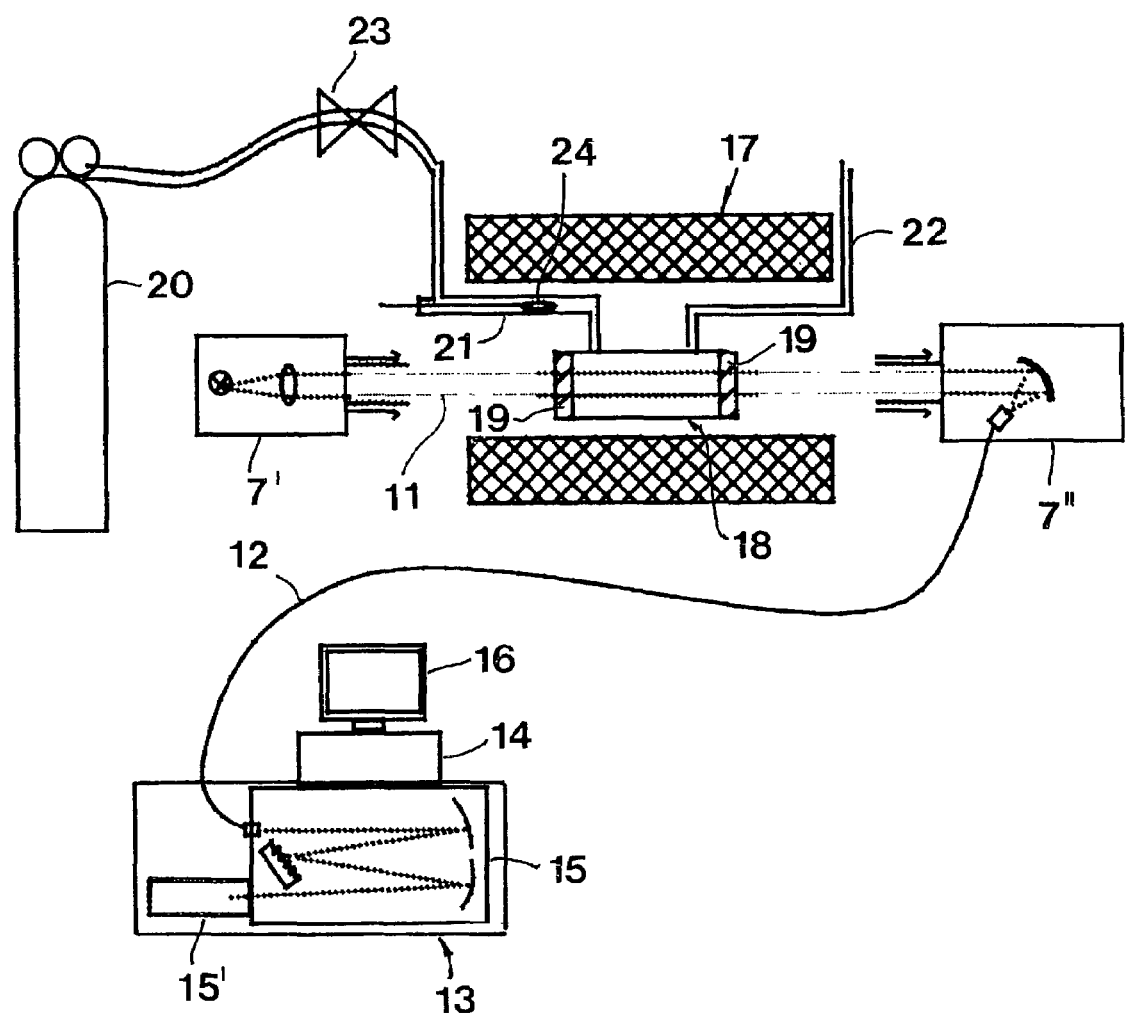
Figure 4:
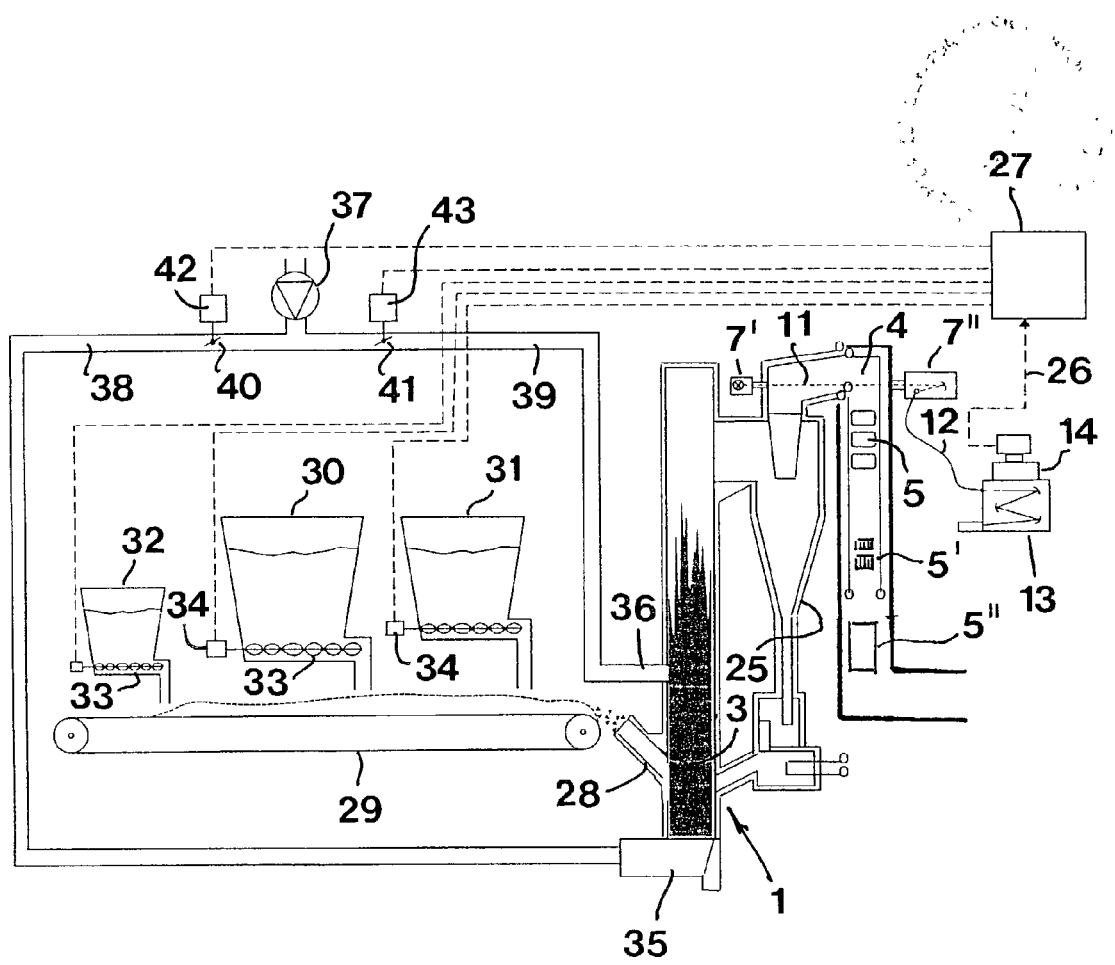

FIG. 1 is a schematic illustration showing the general construction of a combined heat and power plant, in which the invention is applicable, FIG. 2 is an enlarged planar detail view showing a device included in an arrangement according to the invention for sending and receiving light, which device cooperates with a spectrometer, FIG. 3 is a schematic illustration of said spectrometer and an equipment for calibrating the spectrometer, and FIG. 4 is a schematic illustration, shown on a reduced scale, of an alternative embodiment of a combined heat and power plant, and an arrangement according to the invention connected thereto.

DETAILED DESCRIPTION OF THE INVENTION

In FIG. 1 is shown a steam-producing combustion plant that may consist of an industrial steam boiler with the main purpose of producing steam, e.g., for the production of electricity, but that may also consist of a combined power and heating plant of the type that produces not only steam but also heat. As main components, the plant comprises a boiler 1 and a chimney 2. In the boiler 1 is included a first space 3 in the form of a combustion chamber, in which fed-in fuel is burnt. In practice, the boiler may work with conventional fluidized bed technique (among experts called BFB="Bubbling Fluidized Bed"). In larger plants, the boiler may have a height within the range of 10 to 40 meters. In another space 4 serving as a flue gas duct, downstream of the combustion chamber 3, are provided one or several superheater devices. In the example according to FIG. 1, three such superheater devices 5 are shown. Each one of these devices comprises a set of tubes or tube loops, through which steam may pass in order to be overheated by heat transfer from the flue gases that are created during the combustion and that pass through the space 4. Between the spaces 3 and 4 extends an oblique wall 6 included in a separator, whose purpose is to collect solid particles falling down from the flue gases and to return those to the combustion chamber. After the flue gases having passed the superheater devices 5, they are cooled in one or several so-called economizers 5' and pass further through an air pre-heater 5" to finally be emitted via the chimney 2 (usually after first having penetrated through one or several filters, not shown).

In FIG. 1, reference numeral 7 designates a light-emitting and light-receiving device that is comprised in the arrangement according to the invention. As may be clearly seen in FIG. 1, this device 7 is placed in the immediate proximity of a superheater device 5, viz. the superheater device that first comes in contact with the passing flue gases.

Reference is now made to FIG. 2, which illustrates how the device 7 comprises a light-emitting unit 7' that is mounted in one of the two opposite walls 8 that delimit the flue gas duct 4, and a light-receiving unit 7" placed in the opposite wall. As radiation source in the emitting unit 7' is advantageously used a xenon bulb 9, that has the capability of emitting ultraviolet light with a broad wavelength spectrum within the range of about 200 nm–3 μm. Alternatively, a deuterium bulb may also be used for the same purpose. The light from the bulb is collimated, e.g., through a lens 10, whereafter it passes through the flue gases in the duct 4 as a beam 11 and farther into the receiving unit 7", where the light is focused on an optical fiber 12. This optical fiber carries the light to a spectrometer designated 13 in its entirety, in which the intensity of the light is analyzed as a function of the wavelength of the light. A computer 14 cooperates with the spectrometer. In the spectrometer is included a light wavelength separating unit 15, whose purpose is to separate the different wavelengths of the incoming light, so that the intensity of different wavebands may be measured with a non-wavelength-selective detector 15'. In practice, the light wavelength separating unit may consist of a monochromator or a spectrograph. The monochromator lets through only a narrow waveband of the incoming light and may as a wavelength-separating element utilize, e.g., a grating, a prism or an optical band passfilter. The spectrograph projects a continuous band of wavelengths within a given range of wavelengths in its focal plane where the detector is mounted. As a wavelength-separating element in the spectrograph a grating, a prism or a so-called "Michaelson-interferometer" may be used.

For the spectrograph is normally used a multi-channel detector, e.g., a photo-diode array (PDA), or an extended one-channel detector, e.g., a photo multiplicator, in combination with a thin slot that moves sequentially over the surface of the detector and is mounted in such a way that it coincides with the focal plane of the spectrograph. From a practical point of view, this slot may be arranged radially on a rotating disk according to the embodiment described in Platt & Perner 1983 (Platt U & Perner P., "Optical and laser remote sensing", eds. Killinger, D K, and Mooradian, A., "Springer ser". Optical Sci. 39, 97, 1983). The photo-diode array consists of a row of photo diodes (cf. camera) which simultaneously measure the intensity distribution of the light over the surface of the array, whereafter this spectrum is read off electronically after a certain exposing time. In combination with a monochromator, a one-channel light detector is normally used, e.g., a photo diode.

In the embodiment according to FIG. 2, a spectrograph is used in combination with a photo-diode array, which is an advantageous embodiment. The invention may also be realized by utilizing monochromator technique, but in such a case at least two monochromators would be needed, which are adjusted to different wavelengths to make the measuring system specific for the searched gas components, e.g., alkali metal chlorides, and which are not influenced by broad band damping of the light.

The signal from the photo detector is read by means of a specially constructed PC measuring card, and software for PC-Windows, that is especially adapted for the purpose, evaluates the integrated spectrum.

The evaluation of registered measuring spectra in the software of the computer takes place in accordance with the principles suggested in the above-mentioned article by Platt & Perner, 1983. According to algorithms given in this article, quantitative data are calculated for the searched gas components out of the spectral information by correlating measured spectra to referential spectra for different gas components by multivariate analysis. These calculations may be performed continuously in the computer (calculation time <2 s), which enables on-line presentation of measuring data, e.g., on a screen 16, and updating of analogous out-signals on a D/A card in the computer unit.

Among experts, the above described measuring technique is denominated DOAS technique (Differential Optical Absorption Spectroscopy). This technique is also described in general terms in the previously mentioned SE 8502946-0.

The present invention is based on the insight that DOAS technique may be specifically utilized for measuring the concentration of gaseous metals and/or metal chlorides and in particular alkali metal chlorides (potassium chloride as well as sodium chloride) in the flue gases. More specifically, this is realized by calibrating the spectrometer 13 for registration of the spectral intensity distribution of the light within the wavelength range 200–310 nm. For this purpose, a calibration equipment of the type shown in FIG. 3 is used. This equipment comprises an oven 17, in which may be placed a gas cuvette 18 with two quartz windows 19, to which cuvette gas may be led from a source 20 via a supply conduit 21 and evacuated via an evacuation conduit 22. Light-emitting and light-receiving units, respectively, 7', 7" are placed on both sides of the oven, so that the light beam 11 can pass through the cuvette, more precisely via its windows 19. The oven is regulated to a certain temperature, preferably a temperature at which gas-measuring in space 4 is to be performed afterwards. Gas of a given composition containing the gas component, e.g., potassium chloride or sodium chloride, that is intended to be measured in the flue gas duct 4, is dosed from the gas source 20 via a control valve 23 that keeps the gas flow constant, and further through the gas cuvette 18. In the case when potassium chloride or sodium chloride is to be measured, then a salt of the respective compound is placed in a spoon 24, that is introduced into the inlet conduit 21 to the cuvette. By adjusting the temperature of the oven, different vapour pressures are obtained above the salt, and alkali metal chloride vapours with a given partial pressure will stream through the measuring cuvette. When the gas concentration of the gas component in question (and other possible gas components that have light absorption in the wavelength range that shall be utilized for the measuring) has stabilized, then the absorption spectrum of the component is measured and stored according to the same principle as in the regular measuring in the flue gas duct 4. Here, a reference spectrum is obtained that is used as the basis for the automatic spectral evaluation that takes place later when measuring the unknown gas concentration in the flue gas duct.

The spectral structure of KCl and NaCl has such a broad band (=the range of 230–280 nm) and is located at such a wavelength that a simple and inexpensive type of spectrometer may be used for performing the measurement. More precisely, one may advantageously use a modern type of inexpensive minispectrometer that is based on the above-mentioned use of a diode array (semi-conductor sensor) integrated in the optical bench.

Although it is of considerable value per se, only being capable of detecting the concentration in situ of gaseous alkali metal chlorides in the fumes, more specifically continuously during the operation of the plant, it is particularly interesting to utilize registered data to control the course of the fuel combustion. FIG. 4 schematically illustrates a plant in which this possibility has been realized. In this case, an alternative embodiment is exemplified of a combined power and heating plant, in which the boiler 1 of the plant cooperates with a cyclone separator 25 that is installed between the combustion space 3 and the flue gas duct 4 in which a number of superheater devices 5 are mounted (in this example the chimney of the plant has been left out due to spacetechnical reasons). In practice, this type of boiler is denominated CFB (="Circulating Fluidized Bed"). Also in this plant is included at least one economizer 5' and an air pre-heater 5". Similar to the gas measuring arrangement according to FIGS. 1 to 3, the arrangement according to FIG. 4 comprises a light emission unit 7' and a light reception unit 7" that via an optical fiber 12 is connected to a spectrometer 13 and a computer 14 cooperating therewith. Via a cable 26, an out-signal from the computer may be sent to a central control unit designated 27, by means of which different parameters that determine the combustion course may be controlled.

In connection with the fire-place space 3 of the boiler is shown a fuel feed stack 28, to which fuel may be fed by means of a suitable fuel feeder, that is schematically indicated in the form of a conveyor belt 29. Over the conveyor belt are shown a number of containers 30, 31, 32, which either comprise a fuel out-feed means 33, e.g., in the form of a feed screw. In the two former containers 30, 31, two different types of fuel may be kept, e.g., bio-fuel and burnable waste, respectively. In the third container 32 is stored a chlorine-reducing material, which, when needed, may be supplied to the fuel or the fuel mixture to the combustion chamber. Thus, the material in the container 32 constitutes an additive, whose primary purpose is to reduce the amount of alkali metal chlorides in the flue gases. In practice, this substance may consist of sulphur or a sulphur-containing material, although it is also feasible to use minerals, such as kaolinite. The operation of the three out-feed devices may be controlled individually by means of separate control devices 34 that are connected to the central control unit 27. By means of these control devices, the feed devices 33 may on one hand be activated or inactivated in order to initiate or finish the out-feeding of the material in question on the conveyor belt 29, and on the other hand control the working speed of the out-feed device and, thereby, the amount of the respective material that is fed out on the conveyor per time unit.

The so-called air register is also to a high degree determining for the course of the combustion process, which register is included in a conventional way into the combustion plants of the type in question. In practice, such air registers may comprise several consecutive air inlets to the boiler. However, in the example only two such inlets are shown, namely a first inlet 35 for primary air to the lower part of the combustion chamber, and an inlet 36 for secondary air, which is placed downstream of the fuel inlet 28. A central fan 37 may via conduits 38, 39 supply air to the inlets 35, 36, more precisely via flies 40, 41 in the conduits 38, 39. The function of these flies 40, 41 may be controlled by means of separate control means 42, 43, which in turn are controlled by the central control unit 27. Depending on the measurement data in question regarding the existence and concentration, respectively, of alkali metal chlorides in the flue gases, the supply of air to the interior of the boiler may thus be regulated, more precisely in order to reduce the amount of alkali metal chlorides in the region of the superheater arrangements to the utmost possible extent. In this context, it should be pointed out that the relation between the adjusting of the air registers and the content of alkali metal chlorides varies from one plant to another, depending on the design and the combustion principle of the boiler.

FUNCTION AND ADVANTAGES OF THE INVENTION

Initially, the present invention is based on the insight that metal chlorides may be spectral-analyzed with ultraviolet light at high temperatures. By placing the light-emitting and light-receiving units of the described measuring arrangement in the immediate proximity of the superheater device(s) that is/are submitted to corrosion and where the temperature of the flue gases lies within the range of 600 to 1400° C., the existence and concentration of alkali metal chlorides may be established in situ specifically at that place, where the existence of chlorides is critical, namely immediately before they hit the surfaces of the superheater tubes and react with sulphur under the formation of alkali metal sulphate and free chlorine. This is of considerable importance in so far as if gas samples would be taken for extractive analysis, or if measurements would take place downstream of the superheater devices—where the flue gas temperature is lower—then the very reactive chlorides would have the time to condense and/or react with other compounds and, therefore, it would not be possible to measure them in a proper way. Thus, the measurement would entirely lose its relevance if the chlorides had condensed. It should also be underlined that it is also not expedient to measure the chloride content earlier in the process, i.e., in the combustion chamber, in that the chlorides react on their way towards the superheater device. Further, it is of great importance that the survey of the alkali metal chloride concentration in the flue gases of the plant takes place essentially continuously. It is true that it is possible to make individual measurings intermittently, in so far as time breaks between recurrent measuring occasions are allowed. However, by making these breaks short, e.g., within the range of 10 to 60 seconds, an essentially continual survey of the existence and concentration of the corrosion-initiating chlorides is secured. Moreover, by utilizing continually obtained measuring data relative to the chloride concentration in the flue gases, in accordance with the preferred embodiment of the invention, in order to control the combustion process, an effective means is obtained during practical operation for counteracting corrosion attacks on the superheater tubes. Controlling the different parameters that determine the combustion course and the alkali metal chloride amounts developed in the gases may be accomplished in different ways. One effective way is—as described above in connection with FIG. 4—to add a chlorine reducing additive, e.g., in the form of sulphur or a sulphur-containing material. By supplying moderate, albeit effective amounts of sulphur to the fuel, a reaction is attained already during the combustion process between the sulphur and the alkali metal chlorides, thereby, inter alia, forming hydrogen chloride, something that involves that free chlorine is not evolved in the region of the superheater devices. At least the chlorine amounts are reduced in this region to an absolute minimum. Another way is to alter the composition of the fuel mixture, e.g., by reducing the fuel component(s) that turn out to give rise to high contents of alkali metal chlorides. In combination with these measures, the air register may also be adjusted in order to minimize the amount of reactive chlorides in the region of the superheater tubes.

FEASIBLE MODIFICATIONS OF THE INVENTION

The arrangement according to the invention may also be utilized for measuring the existence and concentration of sulphur dioxide ($SO_2$) within the given wavelength range (200 to 310 nanometers), more specifically in order to avoid or counteract overdosing of sulphur additives or sulphur-containing fuels, respectively, or, alternatively, counteract the taking of other operative measures that may increase the $SO_2$ content in the flue gas duct to values above the stipulated limits. It should also be mentioned that the invention may be used for measuring the concentration of other gaseous metal chlorides than just potassium and sodium chlorides, e.g., heavy metal chlorides, such as zinc and lead chloride, respectively, in that also these have a characteristic light absorption within the wavelength range of 200 to 310 nanometers. Within the scope of the invention, it is also feasible to measure the concentration of gaseous metals in elementary form, e.g. elementary zinc. Different existence forms of zinc and lead are foreseen to be present especially frequently in the combustion of waste-related fuels. Zinc and lead chlorides may form ash deposits of a relatively low melting point, e.g., 300° C., on the heat-transferring tube device; this enhances corrosion as well as deposit growth. In particular, they may form deposits on the tubes making part of an economizer. By installing a measuring arrangement according to the invention in the proximity of this type of tube-containing devices, the concentration of these substances may be measured in an appropriate way, whereafter the measuring results may be utilized for taking measures in order to reduce the amount of harmful substances, e.g., by altering the composition of the fuel.

In this context, it may also be mentioned that experts in the field in question attest the theory that a possible existence of dioxines in the fumes is dependent on the amount of alkali metal chlorides. Therefore, within the scope of the invention it is possible to utilize the described measuring arrangement to indirectly—namely by establishing the concentration of alkali metal chlorides—measure the existence and concentration of dioxines that are dangerous to the environment.

It should also be mentioned that the invention may be applied independently of whether the heat-producing plant comprises superheater devices or not. Thus, the invention may, as outlined above, be utilized exclusively for measurements in connection with an economizer or an air pre-heater.

Although the invention in the drawings has been illustrated in connection with two conventional types of combined power and heating plants, viz. plants with fluidized bed boilers of the types BFB and CFB, respectively, it is also applicable on other types of combustion plants, e.g., such that make use of grate firing technique or burners for burning pulverized fuels.

The invention claimed is:

1. A method for measuring the concentration of alkali metal chlorides in flue gases through a heat-producing plant of the kind comprising a first space for combustion of a fuel, a super-heater device placed in a second space located downstream of the combustion space, said superheater comprising tubes through which a medium such as water, air or steam, may pass in order to be heated by heat transfer from the flue gases formed during the combustion, and a chimney located downstream of said super-heater for letting out the flue gases from the plant, the method comprising the steps of:
   locating a UV-light emitter and a UV-light receiver in a region near said super-heater tubing in said second space;
   connecting a photo-spectrometer, in which the light is divided spectrally, to the UV-light receiver;
   calibrating the photo-spectrometer for registering the spectral intensity distribution of received UV-light within the wavelength range of 200 to 310 nanometers;
   detecting, in said second space and in immediate proximity of the super-heater tubing, the concentration of alkali metal chlorides in flue gases at temperatures ranging from 600° C. to 1400° C.; and
   controlling the combustion of the fuel in response to a detected concentration of said alkali metal chlorides in the flue gases,
   wherein the fuel combustion control comprises the step of feeding a metal chloride reducing material into the combustion space.

2. The method as claimed in claim 1, wherein said UV-light emitter and said UV-light receiver are on opposite sides of said gas flow.

3. The method as claimed in claim 1, wherein said step of detecting further comprises detecting gas-phase metals.

4. The device method as claimed in claim 1, wherein said alkali metal chlorides are at least one of NaCl and KCl.

5. A method for measuring the concentration of alkali metal chlorides in flue gases through a heat-producing plant of the kind comprising a first space for combustion of a fuel, a superheater device placed in a second space located downstream of the combustion space, said super-heater comprising tubes through which a medium such as water, air or steam, may pass in order to be heated by heat transfer from the flue gases formed during the combustion, and a chimney located downstream of said super-heater for letting out the flue gases from the plant, the method comprising the steps of:
   locating a UV-light emitter and a UV-light receiver in a region near said super-heater tubing in said second space;
   connecting a photo-spectrometer, in which the light is divided spectrally, to the UV-light receiver;

calibrating the photo-spectrometer for registering the spectral intensity distribution of received UV-light within the wavelength range of 200 to 310 nanometers;

detecting, in said second space and in immediate proximity of the super-heater tubing, the concentration of alkali metal chlorides in flue gases at temperatures ranging from 600° C. to 1400° C.; and controlling the combustion of the fuel in response to a detected concentration of said alkali metal chlorides in the flue gases, wherein the fuel combustion control comprises the step of feeding a sulfur-containing material into the fuel in order to reduce the amount of alkali metal chlorides in the region of said super-heater tubing.

6. A device for measuring the concentration of alkali metal chlorides in flue gases through a heat-producing plant of the kind that comprises a first space for the combustion of a fuel, a super-heater device placed in a second space located downstream of the combustion space, said super-heater in the second space comprising tubes through which a medium, such as water, air or steam, may pass in order to be heated by heat transfer from the flue gases formed during the combustion, and a chimney located downstream of said super-heater for letting out the flue gases from the plant, said measuring device comprising a UV-light emitter located in immediate proximity of the super-heater tubing at one side of said second space;

a UV-light receiver located in immediate proximity of the super-heater tubing at a side of said second space opposite to said UV-light emitter;

a photo-spectrometer connected to the UV-light receiver;

said photo-spectrometer, in which the light is divided spectrally, being calibrated for registering the spectral intensity distribution of received UV-light within the wavelength range of 200 to 310 nanometers, by which measuring device the concentration of said alkali metal chlorides is detectable in flue gases at temperatures ranging from 600° C. to 1400° C. in said second space and in immediate proximity of the super-heater tubing; and a computer unit associated with the photo-spectrometer, said computer unit arranged to generate an out-signal to a control unit for regulating the combustion of the fuel in response to detected concentration of said alkali metal chlorides in the fuel gases, wherein said control unit is connected to a feed device for feeding a metal chloride reducing material into the combustion space.

7. The device as claimed in claim 6, wherein the spectrometer is a diode-array based miniature spectrometer.

8. The device as claimed in claim 6, wherein said control unit is connected to at least one device included in the plant for at least one of feeding in fuel and supplying air to different air registers.

9. The device as claimed in claim 6, wherein said UV-light emitter and said UV-light receiver are on opposite sides of said gas flow.

10. The device as claimed in claim 6, wherein a concentration of gas-phase metals is further detectable by said measuring device.

11. The device as claimed in claim 6, wherein said alkali metal chlorides are at least one of NaCl and KCl.

12. A device for measuring the concentration of alkali metal chlorides in flue gases through a heat-producing plant of the kind that comprises a first space for the combustion of a fuel, a super-heater device placed in a second space located downstream of the combustion space, said super-heater in the second space comprising tubes through which a medium, such as water, air or steam, may pass in order to be heated by heat transfer from the flue gases formed during the combustion, and a chimney located downstream of said super-heater for letting out the flue gases from the plant, said measuring device comprising a UV-light emitter located in immediate proximity of the super-heater tubing at one side of said second space;

a UV-light receiver located in immediate proximity of the super-heater tubing at a side of said second space opposite to said UV-light emitter;

a photo-spectrometer connected to the UV-light receiver;

said photo-spectrometer, in which the light is divided spectrally, being calibrated for registering the spectral intensity distribution of received UV-light within the wavelength range of 200 to 310 nanometers, by which measuring device the concentration of said alkali metal chlorides is detectable in flue gases at temperatures ranging from 600° C. to 1400° C. in said second space and in immediate proximity of the super-heater tubing; and a computer unit associated with the photo-spectrometer, said computer unit arranged to generate an out-signal to a control unit for regulating the combustion of the fuel in response to detected concentration of said alkali metal chlorides in the fuel gases, wherein said control unit is connected to a feed device for feeding a sulfur-containing material into the fuel in order to reduce the amount of alkali metal chlorides in the region of said super-heater tubing.

\* \* \* \* \*